United States Patent [19]
Spinella et al.

[11] Patent Number: 5,968,784
[45] Date of Patent: Oct. 19, 1999

[54] METHOD FOR ANALYZING QUANTITATIVE EXPRESSION OF GENES

[75] Inventors: Dominic G. Spinella, La Costa; Fereydoun G. Sajjadi, Encinitas, both of Calif.

[73] Assignee: Chugai Pharmaceutical Co., Ltd., Tokyo, Japan

[21] Appl. No.: 08/784,208

[22] Filed: Jan. 15, 1997

[51] Int. Cl.$^6$ ............... C12P 19/34; C12N 15/64
[52] U.S. Cl. ............... 435/91.1; 435/6; 435/91.4; 435/91.51; 435/810
[58] Field of Search ............... 435/6, 91.1, 91.2, 435/183, 320.1, 270, 252.3, 91.4, 91.51, 810; 436/94; 935/76, 77; 536/23.1

[56] References Cited

U.S. PATENT DOCUMENTS

| | | | |
|---|---|---|---|
| 4,900,811 | 2/1990 | Sutcliffe | 530/324 |
| 5,242,798 | 9/1993 | Sutcliffe | 435/7.1 |
| 5,508,169 | 4/1996 | Deugau et al. | 435/6 |
| 5,656,425 | 8/1997 | Kraus | 435/6 |
| 5,700,644 | 12/1997 | Gould et al. | 435/6 |

FOREIGN PATENT DOCUMENTS

| | | |
|---|---|---|
| 0234781 | 2/1987 | European Pat. Off. . |
| 0761822 | 3/1997 | European Pat. Off. . |
| 9513369 | 5/1995 | WIPO . |
| 9520681 | 8/1995 | WIPO . |
| 9814619 | 4/1998 | WIPO . |

OTHER PUBLICATIONS

"ZAP Express cDNA Synthesis Kit", #200403, Stratagene, 1995.

"Lambda ZAP Express"—Internet –http://biology.quensu.ca/~miseners/vector_descrip.

Andersson, et al., "Simultaneous Shotgun Sequencing of Multiple cDNA Clones", *DNA Sequence—The Journal of Sequencing and Mapping,* 7(2):63–70.

Brenner and Livak, "DNA fingerprinting by sampled sequencing", *Proc. Natl. Acad. Sci. USA,* 86:8902–8906 (1989).

Cease & Cortland, "A Vector for Facile PCR Product Cloning and Modification Generating Any Desired 4–Base 5'Overhang:pRPM", *BioTechniques,* 14(2):250–255 (1993).

Chollet and Kawashima, "Biotin–labeled synthetic oligodeoxyribonucleotides: chemical synthesis and uses as hybridization probes", *Nucleic Acids Research,* 13(5):1529–1541 (1985).

Fields, et al., "How many genes in the human genome?", *Nature Genetics,* 7:345–346 (1994).

Ghosh and Musso, "Covalent attachment of oligonucleotides to solid supports", *Nucleic Acids Research,* 15(13):5353–5372 (1987).

Gubler and Hoffman, "A simple and very efficient method for generating cDNA libraries", *Gene,* 25:263–269 (1983).

Hasan, et al., "A novel multistep method for generating precise unidirectional deletions using BspMI, a class–IIS restriction enzyme", *Gene,* 50:55–62 (1986).

(List continued on next page.)

*Primary Examiner*—Bradley L. Sisson
*Attorney, Agent, or Firm*—Charles Cappellari; Christine Gritzmacher; Richard A. Hake

[57] ABSTRACT

The present invention provides novel methods for identifying gene expression patterns in mRNA populations. The methods are useful for determining differential gene expression among various cells or tissues, including cells or tissues of a target organism. The invention also provides methods of determining the frequency of gene expression in mRNA populations, thus providing a method of comparing gene expression frequency among various cells or tissues. The present invention also provides methods for isolating genes corresponding to tag sequences identified according to the methods of the present invention. Furthermore, sequences that are identified according to the present invention may be used to diagnose the presence of disease.

47 Claims, 4 Drawing Sheets

OTHER PUBLICATIONS

Ivanova, et al., "Novel Method of Comparative Gene Expression Analysis and Identification of Differentially Expressed mRNAs", *Molecular Biology*, 28(6):848–853 (1995).

Jones, "An Iterative and Regenerative Method for DNA Sequencing", *BioTechniques*, 22(5):938–946 (1997).

Kaiser and Murray, "The Use of Phage Lambda Replacement Vectors in the Construction of Representative Genomic DNA Libraries", *DNA Cloning: A Practical Approach*, Edited by DM Glover, 1:1–48.

Kato, K., "Description of the entire mRNA population by a 3'end cDNA fragment generated by clas IIS restriction enzymes", *Nucleic Acids Research*, 23(18):3685–3690 (1995).

Lee, et al., "Sequential amplification of clone DNA as tandem multimer using class–IIS restriction enzymes", *Genetic Analysis: Biomolecular Engineering*, 13:139–145 (1996).

Maniatis, et al., "The Isolation of Structural Genes from Libraries of Eucaryotic DNA", *Cell*, 15:687–701 (1978).

Mormeneo et al., "Precise nucleotide sequence modifications with bidirectionally cleaving class–IIS excision linkers", *Gene*, 61:21–30 (1987).

Podhajska, et al., "Conferring New Specificities on Restriction Enzymes: Cleavage at Any Predetermined Site by Combining Adapter Oligodeoxynucleotide and Class–IIS Enzyme", *Methods in Enzymology*, 216:303–309 (1992).

Smith, et al., "The synthesis of oligonucleotides containing an aliphatic amino group at the 5' terminus:synthesis of fluorescent DNA primers for use in DNA sequence analysis", *Nucleic Acids Research*, 13(7):2399–2412 (1985).

Szybalski, W., "Universal restriction endonucleases: designing novel cleavage specificities by combining adapter oligodeoxynucleotide and enzyme moieties", *Gene*, 40:169–173 (1985).

Szybalski, et al., "Class–IIS restriction enzymes—a review", *Gene*, 100:13–26 (1991).

Unrau and Deugau, Non–cloning amplification of specific DNA fragments from whole genomic DNA digests using DNA 'indexers', *Gene*, 145:163–169 (1994).

White, et al., "Concatemer Chain Reaction: A Taq DNA Polymerase–Mediated Mechanism for Generating Long Tandemly Repetitive DNA Sequences", *Analytical Biochemistry*, 199:184–190 (1991).

Adams et al., "Complementary DNA Sequencing: Expressed Sequence Tags and Human Genome Project," *Science* 252:1651–1656 (1991).

Adams et al., "Sequence identification of 2,375 human brain genes," *Nature* 355:632–634 (1992).

Aviv and Leder, "Purification of Biologically Active Globin Messenger RNA by Chromatography on Oligothymidylic acid–Cellulose," *Proc. Natl. Acad. Sci. USA* 69:1408–1412 (1972).

Crystal, "Transfer of Genes to Humans: Early Lessons and Obstacles to Success," *Science* 270:404–410 (1995).

Fleischmann et al., "Whole–Genome Random Sequencing and Assembly of *Haemophilus influenzae* Rd," *Science* 269:496–512 (1995).

Fraser et al., "The Minimal Gene Complement of *Mycoplasma genitalium*," *Science* 270:397–403 (1995).

Gilliand et al., "Ch. 8: Competitive PCR for Quantitation of mRNA," in *PCR Protocols: A Guide to Methods and Applications*, Academic Press, Inc., pp. 60–69 (1990).

Goffeau, "Life with 482 Genes," *Science* 270:445–446 (1995).

Hodgkin et al., "The Nematode *Caenorhabditis elegans* and Its Genome," *Science* 270:410–414 (1995).

Kahn, "From Genome to Proteins: Looking at a Cell's Proteins," *Science* 270:369–370 (1995).

Lee et al., "Positive Selection of Candidate Tumor–Suppressor Genes by Subtractive Hybridization," *Proc. Natl. Acad. Sci. USA* 88:2825–2829 (1991).

Liang and Pardee, "Differential Display of Eukaryotic Messenger RNA by Means of the Polymerase Chain Reaction," *Science* 257:967–971 (1992).

Liang et al., "Distribution and cloning of eukaryotic mRNAs by means of differential display: refinements and optimization," *Nucleic Acids Research* 14:3269–3275 (1993).

Nadeau et al., "Multilocus markers for mouse genome analysis: PCR amplification based on single primers of arbitrary nucelotide sequence," *Mammalian Genome* 3:55–64 (1992).

Nowak, "Entering the Postgenome Era," *Science* 270:368–369 and 371 (1995).

Olson, "A Time to Sequence," *Science* 270:394–396 (1995).

Sambrook et al., "Ch. 7—Extraction, Purification, and Analysis of Messenger RNA from lukaryotic Cells," in *Molecular Cloning: A Laboratory Manual, 2nd edition*, vol. 1, Cold Spring Harbor Laboratory Press, pp. 7.1–7.87 (1989).

Sambrook et al., in *Molecular Cloning: A Laboratory Manual, 2nd edition*, vol. 2, Cold Spring Harbor Laboratory Press, p. 9.51 (1989).

Sambrook et al., in *Molecular Cloning: A Laboratory Manual, 2nd edition*, vol. 2, Cold Spring Harbor Laboratory Press, pp. 11.46–11.47, 11.55–11.57 (1989).

Schena et al., "Quantitative Monitoring of Gene Expression Patterns with a Complementary DNA Microarray," *Science* 270:467–470 (1995).

Stratagene Cloning Systems, Product Catalog, p. 312 (1993).

Velculescu et al., "Serial Analysis of Gene Expression," *Science* 270:484–487 (1995).

Welsh and McClelland, "Fingerprinting genomes using PCR with arbitrary primers," *Nucleic Acids Research* 18:7213–7218 (1990).

Welsh et al., "Arbitrarily primed PCR fingerprinting of RNA," *Nucleic Acids Research* 20:4965–4970 (1992).

White et al., "The polymerase chain reaction," *Trends in Genetics* 5(6):185–189 (1989).

Williams, "DNA polymorphisms amplified by arbitrary primers are useful as genetic markers," *Nucleic Acids Research* 18:6531–6535 (1990).

Woodward et al., "Random sequence oligonucleotide primers detect polymorphic DNA products which segregate in inbred strains of mice," *Mammalian Genome* 3:73–78 (1992).

Research Genetics (advertisement), Nucleic Acids Research, vol. 22, No. 15, Aug. 11, 1994.

Sigma Molecular Biology (catalog), pp. 42, 43, and 108, 1989.

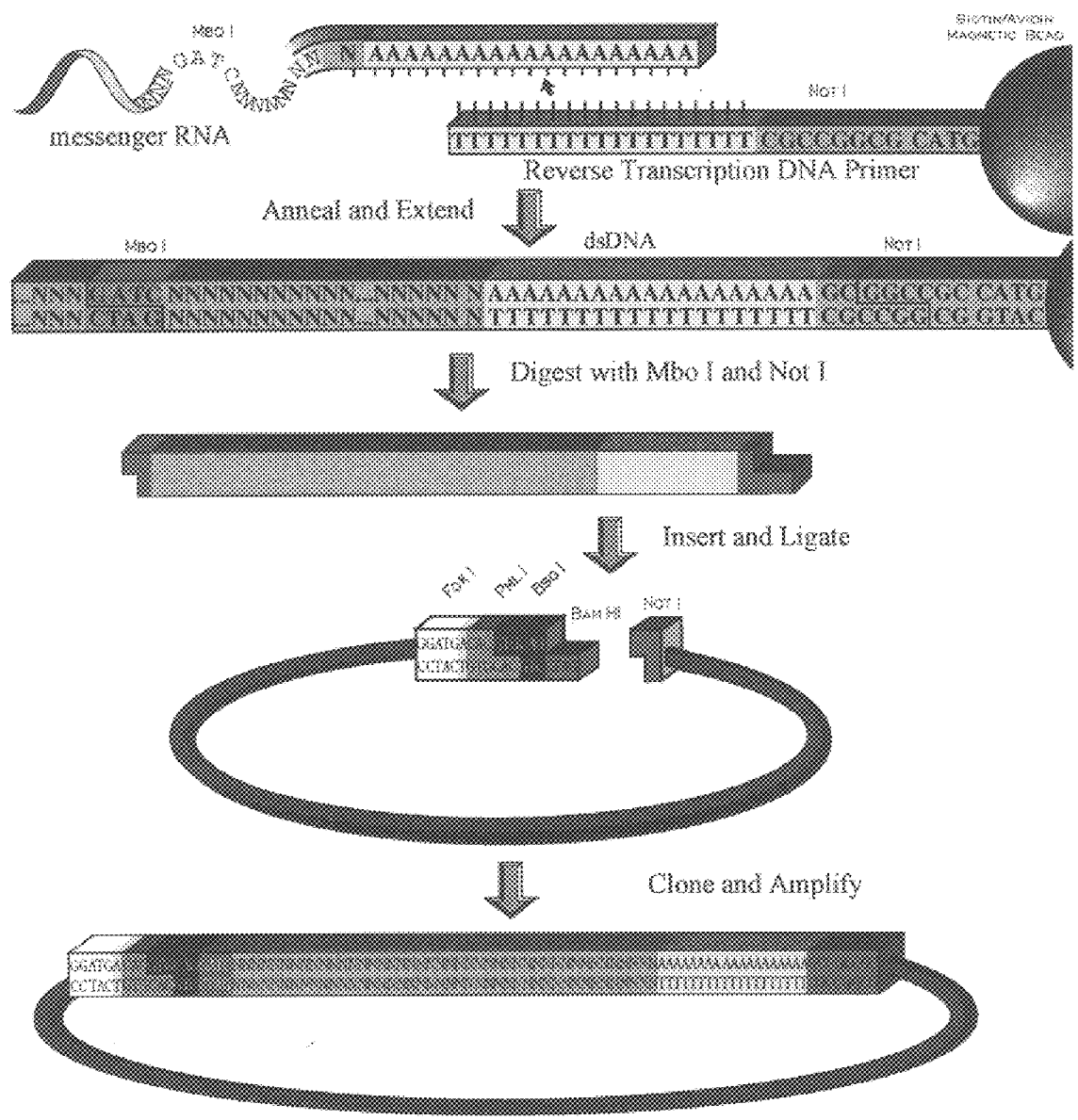

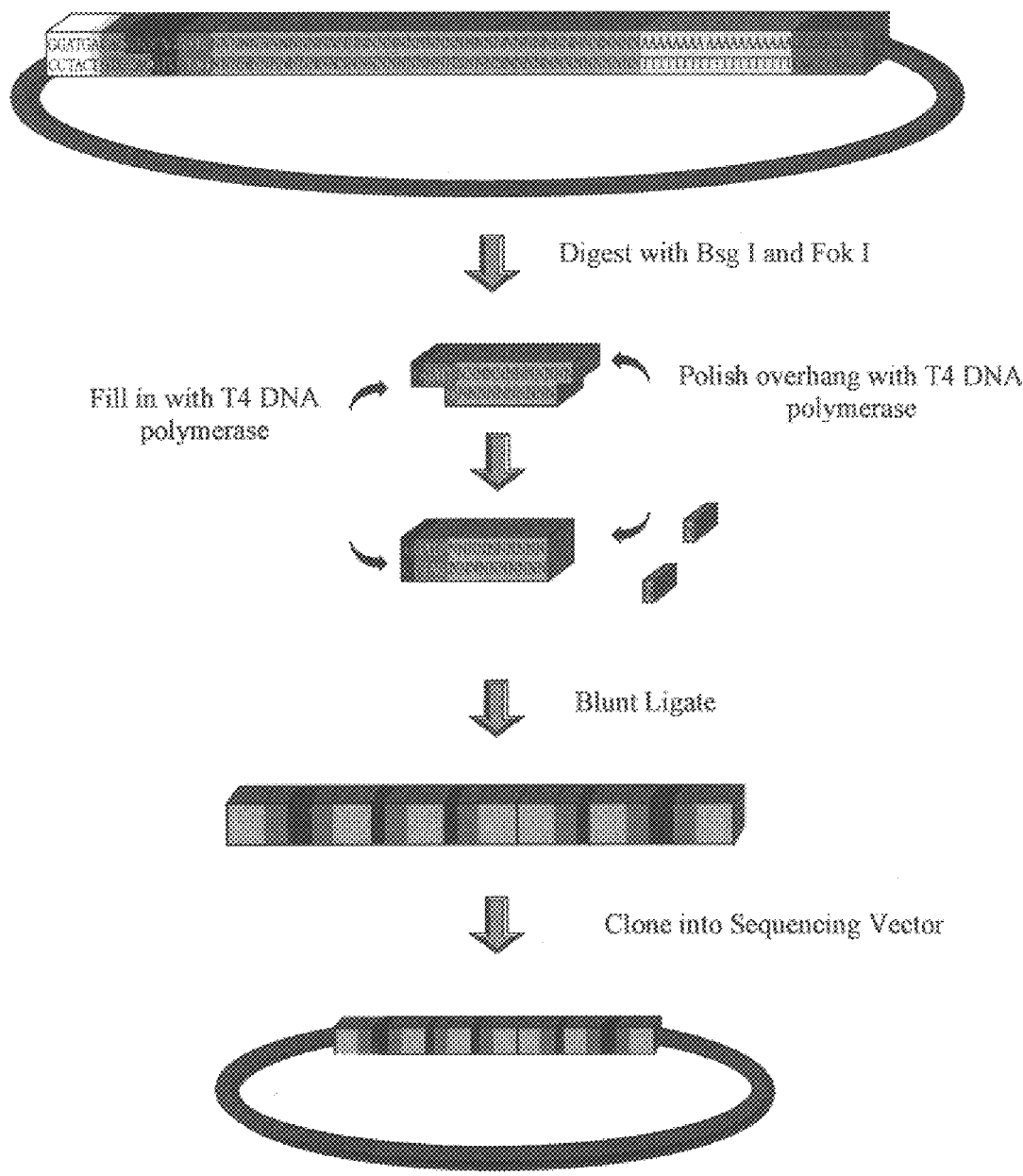

FIGURE 3

5' TTTTTTTTTTTTTTTTTTTTCGCCGGGCGCATG 3'

METHOD FOR ANALYZING QUANTITATIVE EXPRESSION OF GENES

FIELD OF THE INVENTION

The present invention relates to novel methods for identifying gene expression patterns in cells and tissues, methods for determining the frequency of gene expression in cells and tissues, including cells or tissues of a target organism, and vectors used for identifying gene expression patterns. Target organisms include humans, animals and plants. The present invention also provides methods for isolating genes corresponding to tag sequences identified according to the methods of the present invention. The present invention also relates to methods for diagnosing diseases related to differential gene expression and to methods for determining the effects of drugs on gene expression.

BACKGROUND OF THE INVENTION

The human genome contains approximately 100,000 genes, however, in any given cell, only a fraction of these genes are expressed. Thus, in each cell type, only a fraction of human genes are expressed at any one time. Each gene is expressed at a precise time and at a precise level.

Automated DNA sequencers have made it easier to determine the sequence of the genome of an organism; the genomic sequences of *Haemophilus influenzae, Mycoplasma genitalium*, and *Caenorhabditis elegans* have been published leading to the possibility that the genomic sequence of other higher organisms, such as humans, may be obtained (Fleischmann, R. D. et al., *Science,* 269:496, (1995); Fraser, C. M., et al., *Science,* 270:397 (1995); Hodgkin, J., et al., *Science,* 270:410, 1995)). However, the information derived from this technology still does not answer the question of which of these genes are expressed at any one time in any given cell. This information is crucial to determine how cells are differentiated from each other, how cells age, and the causes and effects of many diseases.

A typical mammalian cell of a given lineage expresses approximately 20,000–30,000 of the 100,000 odd germ line genes carried in its genome. Almost all cells constitutively express many of the same genes, which are called "housekeeping" genes. Examples of housekeeping genes include genes encoding enzymes involved in glycolysis or proteins involved in cell structure. However, it is the non-constitutively expressed genes that differentiate cells from each other. As cells mature into differentiated cells, certain non-constitutively expressed genes are turned on and off at different stages. Thus, the differences in gene expression patterns between cells make, for example, a nerve cell different from a blood cell.

Furthermore, the intracellular concentration of a non-constitutively expressed gene product can be modulated by the induction or repression of gene expression in response to environmental signals. Thus, the relative concentration of gene products within a given cell type can be indicative of the state of the cell.

Even within a single cell, the level of expression can vary a great deal from one gene to the next. In a typical cell, there are perhaps 200,000 mRNA molecules which represent 20,000–30,000 different transcribed sequences, present in the cytoplasm. A few of these transcript sequences may be present in high abundance, with thousands of copies or more present per cell. For example, up to 70% of the total mRNA in an antibody secreting plasma cell is represented by immunoglobulin mRNA. Other genes, typically housekeeping genes such as actin or glucose-6-phosphate dehydrogenase, are present at medium abundance with approximately 100–1,000 copies per cell. However, more than 90% of gene transcripts, are present in low abundance at a level of less than 10–15 copies per cell.

Under abnormal cellular conditions such as those in individuals with diseases or disorders, the pattern of gene expression within individual cells may be changed compared to the expression pattern seen under normal non-disease conditions. A change in gene expression may be an effect or the cause of a disease or other abnormality, such as in, for example, a tumor cell. Whereas some diseases may be understood as caused by mutations in particular genes and thus could potentially be detected by examining the genomic sequence, many diseases and disorders involve a malfunction in the level of expression of genes which cannot be detected by sequencing the genome but can only be detected by identifying the gene expression patterns of the cells. Therefore, in order to understand the function of specific cell types in an organism or to understand the progression of disease, it is necessary to understand the expression status of individual genes within these specific cell types at different stages of the organism's development.

One way researchers have attempted to answer these questions is to isolate proteins from various cells and to compare the abundance of each of these proteins. In one approach, proteins are purified from the cells and their abundance is compared. However, this approach is limited by difficulties in devising equally efficient methods of purifying different proteins. This approach is also limited to known proteins. In another approach, two-dimensional gel electrophoresis is used to compare protein expression, but this may lead to difficulties in resolving all of the proteins in the cell and in detecting proteins that are produced at a very low level (See Kahn, P. *Science,* 270:369 (1995)).

Other methods of determining peptide expression in an mRNA population involve the use of antibodies to probe populations of peptides produced from mRNA pools. Thus, "libraries" of synthetic polypeptides corresponding to the polypeptides coded for by mRNA molecules are produced and then probed by individual antibodies. This method does not provide for a detection of all of the polypeptides produced by the mRNA at one time as it may not detect low levels of expression. Moreover, the method is limited to available antibodies. This method is described in, for example, U.S. Pat. No. 5,242,798, issued Sep. 7, 1993, and in U.S. Pat. No. 4,900,811, issued Feb. 13, 1990.

Furthermore, in all of these protein detection methods, once a particular protein difference has been determined, the protein must still be partially sequenced and cloned in order to determine the gene that is responsible for expression of the protein. Alternatively, the protein must be sequenced and compared to a "proteome" database (Kahn, P. *Science,* 270:369, (1995)). Moreover, determining gene expression patterns by looking at purified proteins from the cell is a method of looking at secondary and tertiary effects of gene expression—translation of mRNA into protein, and post-translational modification—and not the primary effect—transcription of DNA sequences into mRNA. Detecting protein expression levels, furthermore, does not take into account the possibility that proteins may be degraded after translation and that the difference in protein expression is not actually due to a difference in gene expression.

Researchers have also focused on detecting changes in expression of individual mRNAs. One method involves subtractive hybridization, but this method does not have sufficient resolution to detect RNAs that are expressed at very low levels. Lee, S. W. et al., Proc. Natl. Acad. Sci. USA 88:2825 (1991). Another method involves a microarray hybridization assay where cDNA is prepared from two mRNA populations, labeled with two different colors, and used to hybridize to microscope slides to which a cDNA library has been fixed; differential hybridization is then identified by determining whether the sample fluoresces (See, Nowak, R., Science, 270:368, (1995); Schena et al., Science 270:467 (1995)). Because much of each mRNA sequence may not be particular to that mRNA sequence, but may also be common among many of the mRNA sequences in a particular cell, researchers have focused on short specific sequences of each mRNA called "tags" which are specific for a particular mRNA in the cell and are sufficient to identify the expression of a particular mRNA. In one such method, randomly chosen cDNA clones are made from mRNAs of a particular tissue. This bulk method of producing cDNAs results in a database of "expressed sequence tags" (Adams, M. D., et al., Science, 255:1651, 1991; Adams, M. D. Nature 355:632–634, 1992). This method of compiling a database of expressed sequence tags fails to provide any information about differential gene expression nor does it determine the frequency of expression of a gene within a cell.

Other methods have focused on using the polymerase chain reaction (PCR) to define tags and to attempt to detect differentially expressed genes. Many groups have used the PCR method to establish databases of mRNA sequence tags which could conceivably be used to compare gene expression among different tissues (Williams, J. G. K., Nucl. Acids Res. 18:6531, 1990; Welsh, J., et al. Nucl. Acids Res., 18:7213, 1990; Woodward, S. R., Mamm. Genome, 3:73, 1992; Nadeau, J. H., Mamm. Genome 3:55, 1992). This method has also been adapted to compare mRNA populations in a process called mRNA differential display. In this method, the results of PCR synthesis are subjected to gel electrophoresis, and the bands produced by two or more mRNA populations are compared. Bands present on an autoradiograph of one gel from one mRNA population, and not present on another, correspond to the presence of a particular mRNA in one population and not in the other, and thus indicate a gene that is likely to be differentially expressed. Messenger RNA derived from two different types of cells is compared by using arbitrary oligonucleotide sequences of ten nucleotides (random 10-mers) as a 5' primer and one of a set of 12 oligonucleotides complimentary to the poly A tail as a 3' "anchor primer." These primers are then used to amplify partial sequences of mRNAs with the addition of radioactive deoxyribonucleotides. These amplified sequences are then resolved on a sequencing gel such that each sequencing gel has a sequence of 50–100 mRNAs. The sequencing gels are then compared to each other to determine which amplified segments are expressed differentially (Liang, P. et al. Science 257:967, 1992; See also Welsh, J. et al., Nucl. Acid Res. 20:4965, 1992; Liang, P., et al., Nucl. Acids Res., 3269 1993).

Another method based on using PCR to detect the expression of mRNAs relies on the use of 12 anchor primers which hybridize to the poly A tract and two restriction endonucleases, one that cleaves at a 4 nucleotide sequence within the cDNA sequence that corresponds to the mRNA, and another restriction endonuclease which recognizes a single site within each anchor primer. The cDNA derived from the mRNA in each of the 12 pools is then inserted into a vector, downstream from a promoter, and used to transform host cells in order to amplify the vector containing the cDNA insert. "cRNA" antisense transcripts are then made, driven by the promoter, which are then amplified using PCR. The PCR reaction is carried out with 16 or more different primers, in 16 different subpools. Thus, with 12 different anchor primers, 192 subpools are required per mRNA sample. The results of the PCR are then resolved on a sequencing gel (WO 95/13369, Published May 18, 1995).

Yet another method to analyze gene expression in cells also relies on PCR. In this method, called SAGE, a cDNA copy of mRNA is made using a poly dT primer which is then biotinylated. The cDNA copy is then made double-stranded and then cut with an "anchoring enzyme" which recognizes a four base pair sequence present in each cDNA. The biotinylated cDNA is then bound to streptavidin beads to remove the rest of the sequence. This results in a cDNA copy of a portion of the 3' end of the messenger RNA linked to a streptavidin bead. The population of cDNAs linked to streptavidin beads is divided in half. Each half is then ligated to one of two oligonucleotide linkers containing a Type IIs restriction endonuclease recognition site. Type IIs restriction endonucleases cleave DNA at a site different than the recognition site. The sequences are cut with the Type IIs restriction endonuclease (the "tagging enzyme"), resulting in cleavage at a site within the cDNA copy of the mRNA sequence. The end of the DNA sequences are made blunt ended and ligated together in pairs, where the tag sequences are linked with one oligonucleotide linker at the 5' end, and the other at the 3' end. These "di-tags" are then amplified with PCR using primers specific to the linkers. The PCR-amplified regions are cleaved with the anchoring enzyme and concatenated together into a series of di-tags punctuated by the sequence of the anchoring enzyme recognition site. This series of di-tags linked together are then cloned into a sequencing vector and sequenced (Velculescu, V. E. et al., Science 270:484 (1995)).

The use of PCR results in problems of reproducibility and requires the use of other complicated steps, including the preparation and annealing of PCR primers, to a method of detecting gene expression patterns. Moreover, these PCR-based methods do not necessarily detect differences in the frequency of gene expression.

The abundance of a PCR product after amplification is influenced by many factors in addition to starting template abundance. Sequence specific differences in "amplification efficiency" are well known to give rise to artifactual differences quantity of PCR product in the absence of real differences in starting template. Moreover, even repetitive amplification of the same template preparation has been reported to produce product yields that can vary by as much as 6-fold (Gilliand et al. in: PCR Protocols. Academic Press, pp 60–69 (1990)). Hence, any PCR-based method that attempts to infer starting template abundance from the quantity of product produced by amplification requires stringent co-amplification controls. In the above cited "SAGE" technique, all cDNA "tags" that happen to have a highly amplifiable sequence will be over represented while those that have "difficult" sequences will be under-represented after the PCR step. The use of "ditags" fails to rectify all of the reliability problems involved in using SAGE to determine starting template abundance. Excluding any ditag that is repetitively isolated fails to eliminate all of the over-represented tag sequences. Artificially enhanced "amplifiability" may be the result of just one of the tags—in which case any ditag containing the individual member would be over-represented. Moreover, this exclusion does nothing about sequences which are artificially under-represented.

Thus, there is a need for a simple and reproducible method for detecting gene expression, identifying genes, and gene expression patterns in individual cells or tissues as well as a method for determining the frequency of gene expression in these cells or tissues.

SUMMARY OF THE INVENTION

The present invention provides a method for tagging and identifying all of the expressed genes in a given cell population. This method thus allows even mRNAs with low copy number to be detected. By comparing gene expression profiles among cells, this method may be used to identify individual genes whose expression is associated with a pathological phenotype. Using high throughput DNA sequencing and associated information system support to analyze such DNA sequencing, the method of the present invention also permits the generation of global gene expression profiles in a reasonable length and time. Thus, the present invention provides a simple and rapid method of obtaining sufficient data to use in an information system known to those of skill in the art to obtain global gene expression profile and identify genes of interest.

The present invention employs novel methods for identifying gene expression patterns in an mRNA population. The preferred use of the novel methods of the present invention is to identify differential gene expression patterns among two or more cells or tissues. Thus, using the methods of the present invention one can identify a gene or genes that are expressed in any given cell type, tissue, or target organism at a different level from that in another cell type, tissue, or target organism. The methods of the present invention may also be used to identify differential gene expression at different stages of development in the same cell-type or tissue-type, and to identify changes in gene expression patterns in diseased or abnormal cells. Furthermore, the invention may be used to detect changes in gene expression patterns due to changes in environmental conditions or to treatment with drugs.

A first aspect of the invention provides for a method for identifying gene expression patterns in an mRNA population, comprising the steps of:

a. preparing double-stranded cDNAs from an mRNA population using a primer;

b. cleaving said double-stranded cDNAs with a first restriction endonuclease which cleaves at a site within said cDNA sequence and not within said primer, to obtain cDNA inserts;

c. inserting said cDNA inserts into the insertion sites of cloning vectors to obtain a DNA construct, wherein said cloning vectors comprise a second restriction endonuclease recognition sequence 5' to said insertion site such that digestion of said DNA construct with said second restriction endonuclease will cleave said DNA construct at a site within the cDNA insert, and a third restriction endonuclease recognition sequence 5' to or overlapping with said second restriction endonuclease recognition sequence;

d. amplifying said DNA constructs;

e. isolating said amplified DNA constructs;

f. digesting said amplified DNA constructs with said second restriction endonuclease;

g. digesting said amplified DNA constructs with said third restriction endonuclease to obtain tags; and h. obtaining the nucleotide sequence of said tags to identify gene expression patterns in said mRNA population.

In preferred aspects, the nucleotide sequence of the tags is obtained by the steps of:

a) ligating said tags to obtain ligated tag arrays of at least about 10 tags;

b) inserting said ligated tag arrays into a sequencing vector; and c) sequencing said ligated tag arrays.

Preferably, the primer used to prime cDNA synthesis consists of an oligo dT sequence linked at the 5' end of said oligo dT sequence to a cleavage site for a "priming" restriction endonuclease. The oligo dT sequence is preferably about 7 to 40 T residues long, more preferably said oligo dT sequence is about 15 to 30 T residues long. Most preferably, said oligo dT sequence is about 19 T residues long.

In order to maximize the number of mRNAs that can be identified using the methods of the present invention, the priming restriction endonuclease should recognize very few sequences. Thus, preferred priming restriction endonucleases recognize sequences consisting of more than six bases. Preferred restriction endonucleases are known to those skilled in the art, however, the priming restriction endonuclease is preferably one that recognizes an 8-base palindromic sequence. More preferably, the priming restriction endonuclease recognizes a sequence comprising at least one CG dinucleotide. Most preferably, said priming restriction endonuclease is NotI.

It is also preferable that the first restriction endonuclease have a high probability of recognizing a sequence within each cDNA. Thus, in preferred aspects of the invention, the first restriction endonuclease recognizes a sequence consisting of less than six bases. More preferably the first restriction endonuclease recognizes a sequence consisting of four bases. Preferred restriction endonucleases are known to those skilled in the art, however, preferably the first restriction endonuclease recognizes a 4-base sequence. Most preferably, the first restriction endonuclease is MboI.

It is also preferred for the methods of the present invention that said second restriction endonuclease cleaves DNA at a site downstream of the recognition site for said endonuclease, such that digestion of the vector with said second restriction endonuclease will result in cleavage of the cDNA insert at a site within the sequences corresponding to the copied mRNA. Preferred restriction endonucleases are known to those skilled in the art, however, preferably, said second restriction endonuclease is a IIs restriction endonuclease. More preferably, the second restriction endonuclease cleaves DNA 10–14 bases 3' to the recognition sequence. More preferably the second restriction endonuclease is a Type IIS restriction endonuclease. Most preferably, the second restriction endonuclease is BsgI.

In other preferred aspects of the present invention, said third restriction endonuclease recognition sequence is within about 20 to 40, more preferably 10 to 15, nucleotides 5' of said second restriction endonuclease cleavage sequence. A cleavage site at a relatively short distance from the second restriction endonuclease cleavage sequence is preferable in order to maximize the number of tags that may be inserted into a sequencing vector. Thus, it is preferred that the third restriction endonuclease recognition sequence is within about 10 to 15 nucleotides 5' of said third restriction endonuclease cleavage site. In one embodiment, the recognition sequence of the third restriction endonuclease overlaps with the recognition sequence of the second restriction endonuclease. Thus, it is preferable that said third restriction endonuclease recognition sequence is within said second restriction endonuclease recognition sequence. It is also preferable that said third restriction endonuclease cleaves the DNA leaving a blunt end. Preferred restriction endonucleases are known to those skilled in the art. Preferably, said second restriction endonuclease is BsgI and said third restriction endonuclease is PmlI. In a more preferred embodiment, said third restriction site is a type IIs site in which the cleavage site is located immediately 5' to said second restriction cleavage site. Most preferably, said third restriction site is FokI.

Thus, in a preferred aspect, a method is provided for identifying gene expression patterns in an mRNA population, comprising the steps of:

(a) preparing double-stranded cDNAs from a mRNA population using a primer, wherein said primer comprises an oligo dT sequence linked at the 5' end of said oligo dT sequence to a NotI cleavage site;

(b) cleaving said double-stranded cDNAs with NotI and with MboI to obtain cDNA inserts;

(c) inserting said cDNA fragments into an insertion site of a cloning vector to obtain DNA constructs, wherein said cloning vectors further comprise a BsgI recognition sequence 5' to the insertion site such that digestion of said DNA construct with BsgI will cleave said DNA construct at a site within the cDNA insert, and said cloning vectors further comprise a FokI recognition sequence which is located 5' to said BsgI recognition sequence;

(d) amplifying said DNA constructs containing said cDNA inserts in a suitable host;

(e) isolating said amplified DNA constructs;

(f) digesting said amplified DNA constructs with BsgI;

(g) digesting said amplified DNA constructs with FokI to obtain tags;

(h) treating said tags with T4 DNA polymerase to obtain blunt ends;

(I) ligating said tags using DNA ligase to obtain ligated tag arrays of at least about 50 tags, more preferably at least about 100 tags. In other preferred aspects, the ligated tag arrays comprise at least about 200 tags.

(j) inserting said ligated tag arrays into a sequencing vector;

(k) sequencing said ligated tag arrays; and (l) comparing the sequences of individual tags within said ligated tag arrays to known gene sequences to identify gene expression patterns in said mRNA population.

Those skilled in the art will recognize that the vector comprising the cDNA fragment, the DNA construct, may be amplified using any method known in the art. Preferably, the construct is amplified in a host cell such as, but not limited to, E. coli by first transforming E. coli with the construct, growing the transformed cells, and isolating the amplified vector from the grown cells.

In preferred aspects, the tags are caused to have blunt 5' and 3' ends. Preferably, said tags are treated with a DNA polymerase after restriction enzyme digestion, such as, for example, T4 DNA polymerase, to obtain tags having blunt 5' and 3' ends. To aid in sequencing the tags, tags are preferably ligated together using DNA ligase. In preferred aspects, the ligated tag sequences comprise approximately 30–60 tags, more preferably approximately 40–50 tags.

In the context of this disclosure, "gene" should be understood to refer to a unit of inheritable genetic material found in a chromosome, such as in a human chromosome. Each gene is composed of a linear chain of deoxyribonucleotides which can be referred to by the sequence of nucleotides forming the chain. Thus, "sequence" is used to indicate both the ordered listing of the nucleotides which form the chain, and the chain which has that sequence of nucleotides. ("Sequence" is used in the same way in referring to RNA chains, linear chains made of ribonucleotides.) The gene includes regulatory and control sequences, sequences which can be transcribed into an RNA molecule, and may contain sequences with unknown function. Some of the RNA products (products of transcription from DNA) are messenger RNAs (mRNAs) which initially include ribonucleotide sequences (or sequence) which are translated into a polypeptide and ribonucleotide sequences which are not translated. The sequences which are not translated include control sequences and may include some sequences with unknown function. The coding sequences of many human genes are discontinuous, having coding sequences, exons, alternating with non-coding sequences, introns. The introns are present in the mRNA molecule as it is transcribed from the DNA, but the introns are removed and the exons spliced together to form mature mRNA. Thus, mature mRNA is mRNA which is suitable for translation, the introns have been removed and usually other modifications made. It should be recognized that small differences in nucleotide sequence for the same gene can exist between different persons, or between normal cells and cancerous cells, without altering the identity of the gene.

For the purposes of this disclosure, the term "gene expression pattern" means the set of genes of a specific tissue or cell type that are transcribed or "expressed" to form RNA molecules. Which genes are expressed in a specific cell line or tissue will depend on factors such as tissue or cell type, stage of development of the cell, tissue, or target organism and whether the cells are normal or transformed cells, such as cancerous cells. For example, a gene may be expressed at the embryonic or fetal stage in the development of a specific target organism and then become non-expressed as the target organism matures. Or, as another example, a gene may be expressed in liver tissue but not in brain tissue of an adult human. The list of factors affecting expression and the examples are not exhaustive; those factors are intended only as illustration.

References herein to a "portion" of a DNA or RNA chain, or of a gene, mean a linear chain that has a nucleotide sequence which is the same as a sequential subset of the sequence of the chain to which the portion refers. In the present disclosure, the term "complementary" has its usual meaning from molecular biology. Two nucleotide sequences or strands are complementary if they have sequences which would allow base pairing (Watson-Crick or Hogstein) according to the usual pairing rules. This does not require that the strands would necessarily base pair at every nucleotide; two sequences can still be complementary with a low level (e.g., about 1–3%) of base mismatch such as that created by deletion, addition, or substitution of one or a few (e.g., up to 5 in a linear chain of 25 bases) nucleotides, or a combination of such changes.

By the term "correspond," as in, for example, cDNA which "corresponds" to mRNA, is meant that at least a portion of one nucleic acid molecule is either complementary or homologous to a second nucleic acid molecule. Thus, a cDNA molecule may correspond to the mRNA molecule where the mRNA molecule was used as a template for reverse transcription to produce the cDNA molecule. Similarly, a genomic sequence of a gene may correspond to a cDNA sequence where portions of the genomic sequence are homologous or complementary to the cDNA sequence.

In another aspect of the invention is provided a method for determining the frequency of gene expression in an mRNA population comprising the steps of:

a) preparing the cloning vectors comprising the cDNA fragments of the invention, thus obtaining a cDNA library;

b) preparing a tag sequence that is of interest, preferably using the methods of the present invention to identify a gene that is differentially expressed; and c) hybridizing the cDNA library with an oligonucleotide probe comprising said tag sequence to determine the frequency of expression of a gene which comprises the tag sequence.

As used above and throughout this application, "hybridize" has its usual meaning from molecular biology. It refers to the formation of a base-paired interaction between nucleotide polymers. The presence of base pairing implies that a fraction of the nucleotides (e.g., at least 80%) in each of two nucleotide sequences are complementary to the other according to the usual base pairing rules. The exact fraction of the nucleotides which must be complementary in order to obtain stable hybridization will vary with a number of factors, including nucleotide sequence, salt concentration of the solution, temperature, and pH.

In referring to hybridization under "stringent conditions", "stringent" should be understood as an empirical term for any one nucleic acid sequence. However, the term indicates that the nature of the hybridization conditions is such that DNA sequences with an exact match for base pairing, or only a small percentage (5–10%) of base mismatch between the two sequences, will form base paired hybrid molecules which are stable enough to allow detection and isolation. On the other hand, two sequences with a higher level of base mismatch will not form such a stable hybrid under the same conditions. One skilled in the art will know that various factors can be altered to modulate the stringency of the conditions, and will understand how to alter those factors to obtain a desired effect. Examples of these factors are temperature, concentration of sodium ion, and concentration of tetramethylammonium chloride or tetraethylammonium chloride. One skilled in the art will recognize that the degree of stringency of a given set of conditions will be affected by characteristics of the DNA or RNA such as G+C content of the molecules, length of the shorter molecule, and location of the mismatches along the molecules. However, one skilled in the art will also know that there exist formulae which allow an estimation of the melting temperature ($T_M$). An example, for DNA, of such a formula for oligonucleotide probes is a function based on variables for sodium ion concentration, G+C content, and probe length. (Sambrook et al., *Molecular Cloning* (1989) at 11.46, the full text of the treatise which is incorporated in its entirety by reference herein). Similar formulas are available for RNA:RNA hybrids and RNA:DNA hybrids. (Id. at 9.51.) In addition, one skilled in the art will know that the effect of mismatches on melting temperature can be estimated, and that melting temperature can be determined empirically for DNA sequences with perfect matching or with mismatches.

Therefore, one skilled in the art would recognize that "stringent conditions" can be readily determined for the claimed DNA sequences using only routine techniques. In this invention, "stringent conditions" should preferably require at least 80% base pairing, more preferably at least 90% or 95% base pairing, still more preferably at least 97% base pairing, and most preferably at least 98% base pairing.

Those of skill in the art will recognize that the hybridization conditions may be varied by varying temperature, salt concentration, and formamide content of the hybridization and washing solutions. In addition, allowances can be made in the conditions for level of possible mismatch, or to provide a higher or lower level of stringency. Also, the proper level of stringency can be determined empirically to provide specific hybridization using the calculated $T_M$ as a starting estimate. For example, the correspondence of $T_m$ and the degree of mismatch may be calculated according to methods known to those skill in the art, as well as according to the methods described in, for example, Sambrook et al., Molecular Cloning (1989) at 11.47, 11.55–57.

The term "probing" is used herein to refer to the method by which a nucleotide sequence, such as one comprising a tag, is used to hybridize to a pool of RNA or DNA. The pool RNA or DNA may be isolated from its natural environment in the cell or tissue, or the pool may be assayed in situ, within the cell or tissue.

In a related aspect, the present invention contemplates a DNA vector used to identify gene expression patterns in an mRNA population, for example, for use in following the methods of the present invention, comprising:

(a) an insertion site;

(b) a restriction endonuclease recognition sequence, Sequence A, 5' to said insertion site wherein said restriction endonuclease has a cleavage site, Sequence B, 3' to said Sequence A;

(c) a restriction endonuclease recognition sequence, Sequence C, 5' to or overlapping with said Sequence A.

Sequence A may be the same as the second restriction endonuclease recognition sequence used in the methods of the present invention described supra. Sequence C may be the same as the third restriction endonuclease recognition sequence used in the methods of the present invention described supra.

The insertion site of the vector preferably is compatible with the ends of the cDNA inserts according to the present invention. The sequences may also be recognized by restriction endonucleases having compatible ends with the priming and the first restriction endonucleases used to obtain the cDNA insert, as long as the use of said endonucleases, and the insertion of said cDNA inserts maintains the integrity of a cleavage site at the first restriction endonuclease site. If only one of the ends is compatible, the cDNA insert may be inserted using blunt end ligation at one of the ends, as known to those skilled in the art. Suitable restriction endonuclease recognition sites to carry out the methods of the present invention may be selected by those skilled in the art. Thus, in preferred aspects, said insertion site has two ends, wherein the first end is compatible with a first insertion restriction endonuclease cleavage site and said second end is compatible with a second insertion restriction endonuclease cleavage site. Said first insertion restriction endonuclease cleavage site is preferably compatible with the first restriction endonuclease cleavage site according to the methods of the present invention. Said second insertion restriction endonuclease cleavage site is preferably compatible with the second restriction nuclease cleavage site according to the methods of the present invention.

In a preferred embodiment, the vector comprises (a) a restriction endonuclease recognition sequence, Sequence A, wherein Sequence A is recognized by a IIs restriction endonuclease such that said restriction endonuclease has a cleavage site, Sequence B, 3' to Sequence A;

(b) a restriction endonuclease recognition sequence, Sequence C, 5' to or overlapping with said first restriction endonuclease recognition sequence;

(c) a restriction endonuclease cleavage site, Sequence D, 3' to Sequence A and 5' to Sequence B, wherein said cleavage site may be cleaved by a restriction endonuclease that recognizes less than six bases; and (d) a restriction endonuclease cleavage site, Sequence E, wherein said cleavage site may be cleaved by a restriction endonuclease that recognizes more than six bases.

Most preferably, the DNA vector is that depicted in FIG. 1.

In other preferred embodiments are provided DNA constructs, comprising the DNA vector described herein, further comprising a DNA insert at the insertion site. Thus, in one such embodiment, the DNA vector of the present invention further comprises a cDNA insert wherein said cDNA insert is inserted at said insertion site and wherein Sequence B is within said cDNA insert.

In this context, a "vector" is an agent into which DNA of this invention can be inserted by incorporation into the DNA of the agent. Thus, examples of classes of vectors can be plasmids, cosmids, and viruses (e.g., bacteriophage). Typically, the agents are used to transmit the DNA of the invention into a host cell (e.g., bacterium, yeast, higher eukaryotic cell). A vector may be chosen based on the size of the insert desired, as well as based on the proposed use of the vector. For preservation of a specific DNA sequence (e.g., in a cDNA library) or for producing a large number of copies of the specific DNA sequence, a cloning vector would be chosen. For transcription of RNA or translation to produce an encoded polypeptide, an expression vector would be chosen. Following transfection of a cell, all or part of the vector DNA, including the insert DNA, may be incorporated into the host cell chromosome, or the vector may be maintained extrachromosomally.

In yet another aspect of the present invention is provided a method for determining the frequency of gene expression in an mRNA population comprising the steps of preparing the DNA constructs comprising the cDNA inserts of the present invention to obtain a cDNA library; preparing an oligonucleotide probe comprising a tag sequence identified according to the methods of the present invention; and probing said cDNA library with said oligonucleotide probe comprising said tag sequence to determine the frequency of expression of a gene which comprises said tag sequence.

In another aspect of the present invention is provided a method for detecting a difference in gene expression between two or more mRNA populations, comprising a) identifying a gene expression pattern from a first mRNA population according to the methods of the present invention.

b) identifying a gene expression pattern from at least one additional mRNA population according to the methods of the present invention; and c) comparing the gene expression patterns obtained in steps a and b, thereby detecting differences in gene expression between said mRNA populations. In preferred aspects, the first mRNA population is obtained from a normal cell or tissue and the additional mRNA population is obtained from a cell or tissue from a target organism having a disease or disorder. In other preferred aspects, the mRNA populations are obtained from cells or tissues at different developmental stages. In yet other preferred aspects, the mRNA populations are obtained from cells derived from different tissues or organs of the same target organism. In other preferred aspects, the mRNA populations are obtained from different target organisms.

The present invention also provides a method for detecting the presence of a disease in a target organism comprising:

a) identifying a gene that is expressed differently in a normal cell or tissue than a cell or tissue from a target organism having a disease or disorder, according to the methods of the present invention, b) isolating the tag sequence of said gene;

c) probing an mRNA population obtained from a first target organism with said tag sequence to determine the level of expression of said gene;

d) probing an mRNA population obtained from a second normal or diseased target organism with said tag sequence to determine the level of expression of said gene; and e) comparing the level of expression of said gene in said first target organism with the level of expression of said gene in said second target organism to detect the presence of a disease in said first target organism.

For purposes of the present invention, the term "target organism" includes any organism from which RNA can be obtained. Those skilled in the art will recognize that the term includes, for example, animals, plants, other eukaryotic cells, and bacteria.

Another aspect of the present invention is a method for screening for the effects of a drug on a cell or tissue. The method of the present invention can be used to compare mRNA gene expression patterns in cells and tissues that have been treated with a drug versus cells and tissues that have not been treated with a drug. The cells or tissues may be from normal target organisms and the side effects of a drug may be tested, or the cells or tissues may be from diseased target organisms with particular disorders to determine whether the drug may change the gene expression profile in the diseased cells.

In other embodiments of the invention are provided methods for isolating a gene, comprising (a) cleaving double-stranded cDNAs with a first restriction endonuclease to obtain cDNA inserts;

(b) inserting said cDNA inserts into the insertion sites of cloning vectors to obtain a DNA construct, wherein said cloning vectors comprise a second restriction endonuclease recognition sequence 5' to said insertion site such that digestion of said DNA construct with said second restriction endonuclease will cleave said DNA construct at a site within the cDNA insert, and a third restriction endonuclease recognition sequence 5' to or overlapping with said second restriction endonuclease recognition sequence;

(c) amplifying said DNA constructs;

(d) isolating said amplified DNA constructs;

(e) digesting said amplified DNA constructs with said second restriction endonuclease;

(f) digesting said amplified DNA constructs with said third restriction endonuclease to obtain tags;

(g) identifying the tag that comprises a portion of the sequence of the gene to be isolated; and (h) isolating said gene.

In preferred aspects, the gene to be isolated is determined by comparing the nucleotide sequence of a tag with known nucleotide sequences to determine which gene to isolate. Those of skill in the art will recognize that known nucleotide sequences may be obtained from any source, and include sources such as sequence databases, such as GenBank.

In yet other embodiments of the invention are provided methods for isolating a gene that is expressed that is expressed at different levels in a first mRNA population compared to a second mRNA population, comprising:

(a) identifying a gene expression pattern from a first mRNA population according to the present invention;

(b) identifying a gene expression pattern from a second additional mRNA population according to the present invention;

(c) comparing the gene expression patterns obtained in steps a and b, thereby detecting differences in gene expression between said mRNA populations;

(d) identifying a gene that is expressed at a different level in said first mRNA population compared to said second mRNA population; and (e) isolating said identified gene.

In another preferred aspect of the invention, a method is provided for isolating a differentially expressed gene, comprising:

(a) obtaining the nucleotide sequence of ligated tag arrays obtained from a first cell type or tissue according to the methods of the present invention;

(b) obtaining the nucleotide sequence of ligated tag arrays obtained from a second cell type or tissue according to the methods of the present invention;

(c) comparing the frequency of expression of the individual tag sequences of said first and second cell types or tissues;

(d) identifying differentially expressed tag sequences in said first cell type or tissue compared to said second cell type or tissue; and (e) identifying a gene corresponding to said differentially expressed tag sequences.

In preferred aspects, said genes are identified by searching a database of RNA or DNA sequences for said differentially expressed tag sequence. In other preferred aspects, said genes are identified by probing a cDNA library with a probe comprising said differentially expressed tag sequences.

In other aspects of the invention are provided isolated DNA sequences for differentially expressed genes identified according to the methods of the present invention.

In yet another embodiment of the invention, kits are provided for use in identifying gene expression patterns in mRNA populations. Such kits may preferably be used in isolating a gene that is differentially expressed following the methods of the present invention.

BRIEF DESCRIPTION OF THE DRAWINGS

FIGS. 2A and 2B are schematic representation of the method for identifying gene expression patterns of the present invention as described in Example 1.

FIG. 3 depicts the sequence of an oligonucleotide primer (SEQ ID NO. 3) that may be used to prime cDNA synthesis in the present invention, comprising an oligo dT sequence linked to a NotI recognition sequence.

DETAILED DESCRIPTION OF THE INVENTION

Figure 1:
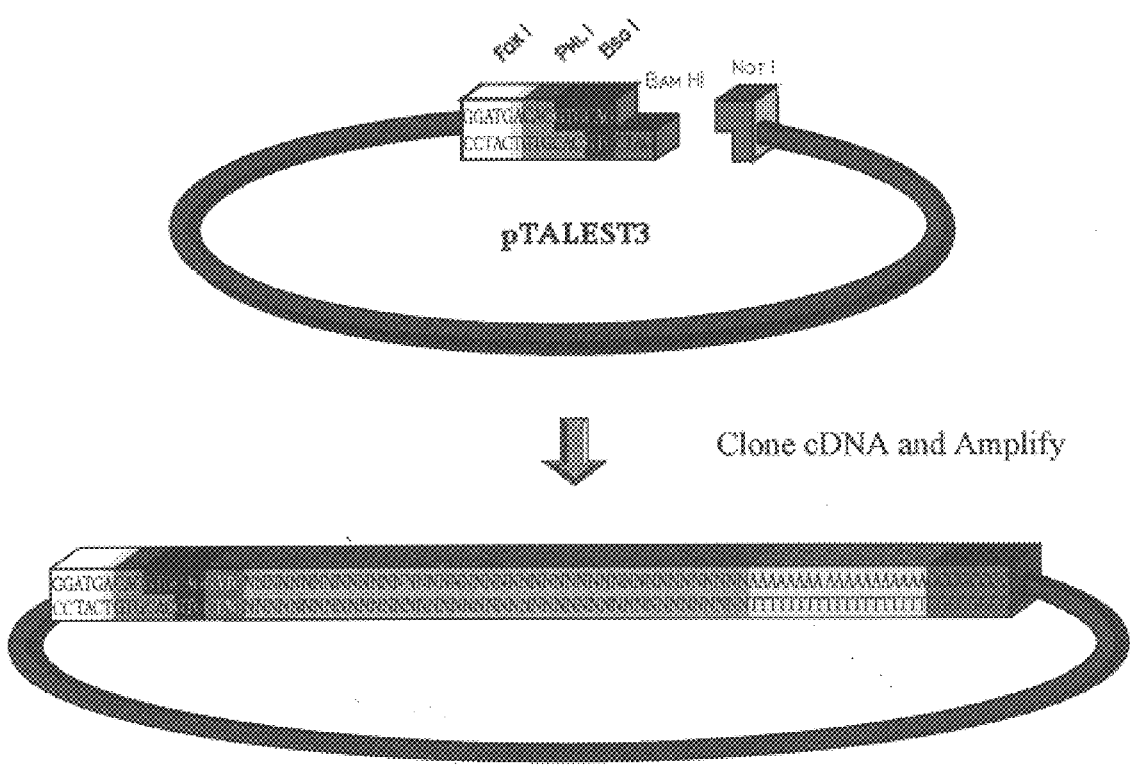
FIG. 1 depicts the TALEST vector (the sequence of the entire vector is submitted as [SEQ ID NO. 1]; the linker sequence depicted is [SEQ ID NO. 2]) used to obtain the tags of the present invention.

In order to fully understand gene expression patterns of a particular cell lineage, it is necessary to know not only which genes are expressed by the cell, but also the frequencies or rates at which they are expressed. The methods of the present invention provide novel methods for identifying gene expression patterns in cells and tissues and methods for determining the frequency of gene expression in cells and tissues in a simple and reproducible manner that does not require the use of PCR or other methods that may limit the reproducibility of the assays. Furthermore, the methods of the present invention are not limited by the ability of the researcher to synthesize numerous oligonucleotide primers to correspond to the huge variety of mRNA sequences. By obtaining the RNA sequence tags according to methods of the present invention, the frequency of gene expression can be determined merely by analyzing the frequency of cDNA expression in the cDNA library prepared during the process of producing the tags.

An overview of the methods of the present invention is presented in FIG. 2. Although the overview presented in FIG. 2 as well as described herein provides a detailed description of the invention using particular restriction endonucleases, and a defined vector, it is well known to those of skill in the art that other restriction endonucleases may be selected and other methods of molecular biology, such as those described in Sambrook J. et al., "Molecular Cloning: A laboratory Manual", Second Ed. (Coldspring Harbor Laboratory Press, Cold Spring Harbor, N.Y., 1989, Volume 1, Chapter 7) incorporated herein by this reference, may be used to practice the present invention and this invention is not limited to the detailed examples presented herein.

Polyadenylated mRNA is first isolated from the cell population of interest using standard procedures. The mRNA is then converted to cDNA using reverse transcriptase by priming the mRNA with an oligo dT sequence that has a rare cutting enzyme site (NotI) at its 5' end. The first strand cDNA is converted to double-stranded cDNA using RNAase H and DNA polymerase 1. The double-stranded cDNA is then digested with two different restriction enzymes, NotI and MboI. The use of two restriction enzymes allows the cDNA to be directionally cloned into the TALEST vector depicted in FIG. 1.

The TALEST vector contains a Bam H1 site, which cleaves ends compatible with MboI digested DNA, and a NotI site. MboI has a four base recognition sequence (GATC) which occurs in eukaryotic DNA on an average of once every 256 base pairs. Thus, the average size of the cloneable NotI/MboI cDNA fragment is approximately 300 base pairs including the portion of the poly A tail that has been cloned. When the cDNA is cloned into the TALEST vector, a cDNA library is formed that is representative of virtually all the expressed genes in the cell.

The library is prepared in a directional orientation such that the 5' terminus of every cDNA in the library always begins with the MboI recognition sequence, the GATC sequence, which in turn is derived from the 3' most MboI site found in the gene. The library is then amplified by transforming the plasmid into a host cell and allowing the bacteria to grow.

The TALEST vector has a BsgI restriction endonuclease site located immediately 5' to the GAT sequence that begins every cDNA. BsgI is a Type IIs restriction endonuclease which recognizes a defined sequence (GTGCAG) but cleaves the DNA approximately 16 bases "downstream" (3') from the recognition sequence. Thus, cleavage of the TALEST vector with BsgI linearises the circular plasmid by cleaving the inserted cDNA 12 bases downstream from the GATC start sequence on the sense strand, and 10 bases on the antisense strand. Because BsgI leaves a 3' "overhang," the unpaired two bases on the sense strand are removed using T4 DNA polymerase to generate blunt ends.

Nine bases upstream from the BsgI site is a second type IIs restriction site, FokI. This enzyme recognizes the 5-base sequence GGATG but cleaves 9 bases downstream (3') on the sense strand, and 13 bases downstream on the antisense strand. When the resultant fragment is subjected to treatment with T4 DNA polymerase, a blunt-ended 15 base "tag" is generated with the sequence: GGATCNNNNNNNNNN (SEQ ID NO.4).

Alternatively, PmlI may be used as the second restriction site. This site is convenient because its recognition sequence (CACGTG) overlaps that of BsgI and it cleaves both the sense and antisense strands of the DNA at the same place leaving blunt ends. Digestion of the BsgI linearized plasmid with Pml1 cleaves off the 20 base blunt ended fragments with the sequence GTGCAGGATCNNNNNNNNNN (SEQ ID NO.5) where the first six bases are derived from the TALEST vector and the next 14 (GATCNNNNNNNNNN) are derived from the cDNA (SEQ ID NO.6).

When the entire amplified cDNA library is digested with BsgI and FokI, a 20 base pair fragment is excised which consists of a mixture of "tags," each of which differs in the sequence of the final ten bases and each of which uniquely mark a single expressed gene. With ten bases of unknown sequence, there are $4^{10}$ or 1,048,576 possible different tag sequences. This number exceeds by approximately five-fold the number of expressed genes in the human genome in all tissues.

The tags are mixed together and subjected to enzymatic treatment with DNA ligase in order to generate tandem arrays of about 30–60, preferably about 40–50 tags in a single molecule. The arrays are then cloned into a sequencing vector and subjected to automated DNA sequence analysis. When the arrays are analyzed, individual tags are recognized because they are separated from each other by the defined punctuation sequence, GGATC (containing the MboI recognition sequences) or its reverse compliment depending on the random sense or antisense or orientation of the tag during ligation.

Each tag begins with the defined GGATC sequence derived from the 3' most MboI site in the original cDNA, and has ten additional bases of unknown sequence that uniquely marks one of the expressed genes in the cell population under study. The presence of the GGATC start sequence effectively provides five bases of additional identifying information, and localizes the information to a particular site within the tagged gene. Thus, in effect, 15 bases of sequence are known for each mRNA that has been copied into cDNA and is analyzed in the present method.

Automated high throughput DNA sequencers known to those of skill in the art allow simultaneous sequence determination of the tags. Thus, this method provides a simple and rapid way of producing tags that can be easily and quickly analyzed using high throughput DNA sequencers. Furthermore, because the present method involves the initial generation of a cDNA library, that library can be probed with an oligonucleotide corresponding to any tag of interest to determine the frequency of expression of the gene identified by the tag. For example, if a given tag shows up three times in a tumor cDNA pool but not at all in the normal cell pool, both cDNA libraries could be probed with a tag to ascertain their exact frequencies. A full length gene could then be isolated and identified using cloning methods known to those of skill in the art.

EXAMPLES

To assist in understanding the present invention, the following Examples are included which describes the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

Example 1

Isolation of mRNA

Methods of extraction of RNA are well known in the art and are described, for example, in Sambrook J., et al., "Molecular Cloning: A Laboratory Manual", Second Ed. (Coldspring Harbor Laboratory Press, Cold Spring Harbor, N.Y., 1989, Volume 1, Chapter 7, incorporated herein by this reference. Other isolation extraction methods are also well known. Isolation is particularly performed in the presence of chaotropic agents such as guanadinium chloride or guanadinium isothiocyanate, other detergents and extraction agents can alternatively be used. It is desirable, but not required, that the messenger RNA be isolated from the total extract RNA by chromatography over an oligo (dT)-cellulose column or other, chromatographic media that have the capability of binding the polyadenylated 3' portion of the mRNA molecules.

Briefly, cells are lysed in RNA extraction buffer [0.14 M NaCl, 1.5 mM $MgCl_2$, 10 mM TrisHCl (pH 8.6), 0.5% NP-40, 1 mM DTT, 1000 units/ml RNase inhibitor (Pharmacia)] by using a Vortex mixer for 30 sec and then left standing on ice for 5 min. Nuclei and other cell debris were precipitated by centrifuging at 12,000 g for 90 sec, and the supernatant was deproteinized with Proteinase K followed by phenol extraction. RNA was precipitated by isopropanol and rinsed with 70% ethanol. Finally, the poly A+ fraction was collected by oligo dT column fractionation (Aviv, D. P., et al., Proc. Natl. Acad. Sci. USA 69, 1408–1412 (1972)).

Example 2

Preparation of Double Stranded cDNA

Double stranded cDNA is then prepared from the mRNA population using a DNA primer of the sequence depicted in FIG. 3. The anchor primer includes a tract of T residues (approximately 7–40 T residues) and a site for cleavage by a restriction enzyme which recognizes more than 6 bases, the site for cleavage being located to the 5' site of the tract of T residues, such as NotI. The cDNA reaction is carried out under conditions that are well known in the art. Such techniques are described in, for example, Volume 2 of J. Sambrook et al., "Molecular Cloning: A Laboratory Manual., Second Ed.". In these methods, one way to carry out this method is by using reverse transcriptase from avion myeloblastosis virus.

The second cDNA strand synthesis may be performed using the RNAase H/DNA polymerase I self priming method. Briefly, two micrograms each of the cytoplasmic Poly $A^+$ RNA and the vector primer DNA were co-precipitated in 70% ethanol containing 0.3 M Na-acetate and the pellet was dissolved in 12 $\mu$l of distilled water. For the first strand synthesis, after heat denaturation at 76° C. for 10 min, 4 $\mu$l of 5×reaction buffer (250 mM Tris-HCl (pH 8.3), 375 mM KCl, 15 mM $MgCl_2$), 2 $\mu$l of 0.1 M DTT, 1 $\mu$l of 10 mM each of dATP, dCTP, dGTP and dTTP were added to the sample at 37° C. The reaction was initiated by the addition of 200 units of reverse transcriptase MMLV-H-RT (BRL), and after incubation at 37° C. for 30 min, stopped by transferring the reaction tube onto ice. For the second strand synthesis, to the aforementioned reaction mixture were added 92 $\mu$l of distilled water, 32 $\mu$l of 5× *E. coli* reaction buffer (100 mM Tris-HCl (pH 7.5), 20 mM MgCl$_2$, 50 mM (NH4)$_2$SO$_4$, 500 mM KCl, 250 g/ml of BSA, 750 M βNAD), 3 μl of 10 mM each of dATP, dCTP, dGTP and dTTP, 15 units of *E. coli* ligase (Pharmacia), 40 units of *E. coli* polymerase (Pharmacia), and 15 units of RNase H (Pharmacia), which was then incubated at 16° C. for 2 h. The reaction mixture was heated to 65° C. for 15 min.

The cDNA sample is then cleaved with MboI and NotI. The cDNA vector sample is then inserted into the TALEST vector depicted in FIG. 2. The TALEST vector has similarly been digested with Bam H1 and NotI using methods known to those skilled in the art. Briefly, a sample containing blank cDNA inserts and blank vector is diluted to up to one ml with 1×*E. coli* reaction buffer, and 100 units of *E. coli* ligase are added. The resulting mixture is incubated at 16° C. overnight. Following insertion of the cDNA, the vector mixture is then used to transform *E. coli* competent cells. Suitable host cells for cloning are described in, for example, Sambrook et al., "Molecular Cloning: A Laboratory Manual". The host cell is grown to increase or amplify the number of vectors produced. A suitable *E. coli* strain is DH5 or MC1061.

Example 3

Generation of Tags

The vectors are isolated from the grown host cell using methods known by those skilled in the art, such as those described for "minipreps," described in, for example, J. Sambrook et al., "Molecular Cloning: A Laboratory Manual., Second Ed." The vectors are then cleaved with BsgI which linearizes the plasmid at a site 12 bases downstream from the MboI start sequence on the sense strand and 10 bases on the antisense strand. T4 DNA polymerase is then used to generate blunt ends on the vector. The vectors are then cleaved with PmlI which results in a 20 base blunt ended fragment with the sequence GTGCAG-GATCNNNNNNNNNN. The tags are separated from the remainder of the vector using polyacrylamide gel electrophoresis as described in, for example, Sambrook et al., supra.

Example 4

Sequencing of Tags

The tags generated in Example 3 are mixed together and subjected to enzymatic treatment with DNA ligase in order to generate tandem arrays of 30–40 tags in a single molecule. To isolate lengths of 30–40 tags, DNA sequences of approximately 420–560 nucleotides in length are isolated by agarose gel electrophoresis as described in, for example, Sambrook et al., supra. The arrays of 30–40 tags are then cloned into a sequencing vector. Suitable sequencing vectors are known to those of skill in the art. One example of an appropriate sequencing vector is pUC19. The sequencing vector containing the tags is then subjected to automated DNA sequence analysis.

Example 5

Determination of Frequency of Gene Expression by Probing cDNA Libraries with Tag Sequences If a particular sequence tag appears to be over or under represented in any individual collection of tags, the actual frequency of the gene from which the tag was isolated may be determined by probing the parent cDNA library. Standard methods known to those skilled in the art may be used to probe the parent cDNA library. For example, prior to isolation of bacterial colonies for plasmid isolation and tag generation, the plates containing said colonies can be overlaid with a nitrocellulose or nylon membrane to generate a replica copy. Alternatively, a new cDNA library from the same tissue source can be produced in either plasmid or phage vectors and expose to filters as described above. The filters are then exposed to a synthetic oligonucleotide probe having the same sequence as the tag of interest. The probe is first labeled with $^{32}$P using standard techniques as described in J. Sambrook et al., "Molecular Cloning: A Laboratory Manual., Second Ed. and other sources. Filters are then washed and exposed to X-ray film. By counting the number colonies or plaques which hybridize to the probe and dividing that number by the total number of clones in the screened library, one obtains a frequency estimate of the transcript prevalence in the tissue from which the library was derived.

Example 6

Cloning of Differentially Expressed Genes

The methods of the present invention may be used to isolate differentially-expressed genes. Particular relatively over-expressed genes may be identified and isolated. By comparing tag frequencies in different libraries derived from related tissues (for example, a tumor and the normal tissue from which it arose) it is possible to identify tags corresponding to genes that are over- or under- expressed in one of the tissues and may be responsible for a pathological or other phenotype of either tissue. In order to more fully characterize these "differentially expressed" genes, one can search the tag sequence against an appropriately filtered database of human RNA or cDNA sequences. Alternatively one can use the tag sequence as a hybridization probe as described in Example 5 to identify full-length clones from a cDNA library. These clones can then be sequenced and searched for homologies to known genes using standard procedures.

---

We claim:

1. A method of identifying gene transcription patterns in an mRNA population, comprising the steps of:
    (a) preparing double-stranded cDNAs from an mRNA population using a primer, wherein said primer contains a recognition sequence of six bases or greater for a priming restriction endonuclease;
    (b) cleaving said double-stranded cDNAs with:
        a first restriction endonuclease which cleaves within said cDNA sequence and not within said primer, and
        the priming restriction endonuclease which cleaves within said primer to obtain a population of cDNA inserts;
    (c) inserting said cDNA inserts into insertion sites of cloning vectors to obtain a population of DNA constructs, wherein said cloning vectors comprise
        a second restriction endonuclease recognition sequence located 5' to said insertion sites, and
        a third restriction endonuclease recognition sequence located 5' to or overlapping with said second restriction endonuclease recognition sequence,
and wherein said cDNA inserts are inserted into said cloning vectors in an orientation in which an end cleaved by the first restriction endonuclease is proximal to the second restriction enzyme recognition site and an end cleaved by the primer restriction endonuclease is distal to the second restriction enzyme recognition site;
    (d) replicating said DNA constructs;
    (e) isolating said DNA constructs;
    (f) digesting said DNA constructs with a second restriction endonuclease that is a Type IIs restriction endonuclease, thereby cleaving within the cDNA inserts;
    (g) digesting said DNA constructs with a third restriction endonuclease, thereby cleaving the DNA constructs 5' to cleavage sites of the second restriction endonuclease to obtain tags comprising cDNA sequences;
    (h) causing said tags to have blunt 5' and 3' ends, if one or more ends has an overhang resulting from restriction endonuclease digestion;
    (i) ligating said tags to obtain ligated tandem arrays of tags comprising at least 10 tags;
    (j) inserting said ligated tandem arrays of tags into a sequencing vector; and
    (k) determining the nucleotide residue sequence of said tags to identify gene transcription patterns in said mRNA population.

2. The method of claim 1 wherein said DNA constructs are amplified in a host cell capable of replicating said DNA constructs.

3. The method of claim 2 wherein said host cell is *E. coli*.

4. The method of claim 1 wherein said first restriction endonuclease recognizes a sequence consisting of less than six bases.

5. The method of claim 1 wherein said first restriction endonuclease recognizes a sequence consisting of four bases.

6. The method of claim 5 wherein said first restriction endonuclease is MboI.

7. The method of claim 1 wherein said third restriction endonuclease is PmlI or FokI.

8. The method of claim 1, wherein said second restriction endonuclease is BsgI.

9. The method of claim 1 wherein said third restriction endonuclease recognition sequence is located within 20 to 40 nucleotides 5' of a cleavage site of said second restriction endonuclease.

10. The method of claim 1 wherein said third restriction endonuclease recognition sequence is located within 10 to 15 nucleotides 5' of a cleavage site of said second restriction endonuclease.

11. The method of claim 10 wherein said second restriction endonuclease is BsgI and said third restriction endonuclease is FokI.

12. The method of claim 1 wherein said third restriction endonuclease recognition sequence is located within said second restriction endonuclease recognition sequence.

13. The method of claim 12 wherein said second restriction endonuclease is BsgI and said third restriction endonuclease is PmlI.

14. The method of claim 1 wherein said primer comprises an oligo dT sequence.

15. The method of claim 14 wherein said oligo dT sequence consists of 7 to 40 T residues.

16. The method of claim 14 wherein said recognition sequence for a priming restriction endonuclease is linked to the 5' end of said oligo dT sequence.

17. The method of claim 16 wherein said priming restriction endonuclease recognizes a sequence consisting of more than six bases.

18. The method of claim 17 wherein said priming restriction endonuclease recognizes a sequence consisting of at least 8 bases.

19. The method of claim 18 wherein said priming restriction endonuclease recognizes a sequence comprising at least one CG dinucleotide.

20. The method of claim 1, wherein said priming restriction endonuclease is Not I.

21. The method of claim 1 wherein insertion sites of said cloning vectors have a first end compatible with a cleavage site of said priming restriction endonuclease and a second end compatible with a cleavage site of said first restriction endonuclease.

22. The method of claim 1 wherein said tags are treated with T4 DNA polymerase to cause tags to have blunt 5' and 3' ends.

23. The method of claim 1 wherein said ligating step uses DNA ligase.

24. The method of claim 1 wherein said ligated tandem arrays of tags comprise at least 50 tags.

25. The method of claim 1 wherein said ligated tandem arrays of tags comprise at least 100 tags.

26. The method of claim 1 wherein said ligated tandem arrays of tags comprise at least 200 tags.

27. A method for determining the frequency of gene transcription in an mRNA population comprising the steps of:
    (a) preparing a cDNA library comprising DNA constructs according to steps (a) through (d) of claim 1;
    (b) preparing an oligonucleotide probe comprising a nucleotide sequence of a tag identified according to the method of claim 1; and
    (c) probing said cDNA library with said oligonucleotide probe to determine the frequency of transcription of a gene which comprises said nucleotide sequence.

28. The method of claim 27, further comprising the step of isolating from said cDNA library a gene sequence which comprises said nucleotide sequence for which the frequency of gene transcription was determined in step (c).

29. A method for detecting a difference in gene transcription between two or more mRNA populations, comprising the steps of:
    (a) identifying a gene transcription pattern from a first mRNA population according to claim 1;
    (b) identifying a gene transcription pattern from at least one additional mRNA population according to the method of claim 1; and
    (c) comparing the gene transcription pattern of said first mRNA population with the gene transcription pattern of at least one additional mRNA population, thereby detecting differences in gene transcription between said first and additional mRNA populations.

30. The method of claim 29 wherein said first mRNA population is obtained from a normal cell or tissue and said additional mRNA population is obtained from a cell or tissue from a target organism having a disease or disorder.

31. The method of claim 30, further comprising the step of isolating a tag nucleotide sequence that is differentially expressed in said first mRNA population compared to said additional mRNA population to produce a probe containing said tag nucleotide sequence.

32. The method of claim 31, further comprising the steps of:

probing a second additional mRNA population with said probe containing said tag nucleotide sequence to determine gene transcription of said tag nucleotide sequence in said second additional mRNA population; and determining whether gene transcription of said tag nucleotide sequence in said second additional mRNA population is similar to the gene transcription pattern on said first mRNA population obtained from a normal cell or tissue or similar to the gene transcription pattern of the additional mRNA population obtained from a cell or tissue from a target organism having a disease or disorder.

33. The method of claim 26 wherein said first and said additional mRNA populations are obtained from cells or tissues at different developmental stages.

34. The method of claim 29 wherein said first and additional mRNA populations are obtained from cells derived from different tissues or organs of a single target organism.

35. The method of claim 29 wherein said first and said additional mRNA populations are obtained from different target organisms.

36. The method of claim 29, further comprising the step of isolating a tag nucleotide sequence that is differentially expressed in said first mRNA population compared to said additional mRNA population to produce a probe containing said tag nucleotide sequence.

37. The method of claim 36, further comprising the step of probing a second additional mRNA population with said probe containing said tag nucleotide sequence to determine a gene transcription pattern of said tag nucleotide sequence in said second additional mRNA population.

38. The method of claim 36, further comprising the step of probing a cDNA library with the probe containing said tag nucleotide sequence to isolate a gene sequence that hybridizes to said tag nucleotide sequence.

39. A kit for use in identifying gene transcription patterns in an mRNA population, comprising:

(a) a DNA vector comprising an insertion site that includes a NotI recognition sequence, a first restriction endonuclease recognition sequence, Sequence A, located 5' to said insertion site, wherein said first recognition sequence is specific for a first restriction endonuclease that cleaves at a site, Sequence B, located 3' to said first recognition sequence, and a second restriction endonuclease recognition sequence, Sequence C, located 5' to or overlapping Sequence A;

(b) a primer comprising an oligo dT sequence of 7 to 40 T residues;

(c) a first restriction endonuclease that recognizes said Sequence A and cleaves DNA at a said Sequence B; and (d) a second restriction endonuclease that recognizes said Sequence C.

40. The kit of claim 39, wherein said primer further comprises a cleavage site of a priming restriction endonuclease linked to the 5' end of said oligo dT sequence.

41. The kit of claim 40, wherein said priming restriction endonuclease recognizes a sequence of at least 8 bases.

42. The kit of claim 39, wherein said first restriction endonuclease is a Type IIS restriction endonuclease.

43. The kit of claim 39, wherein said second restriction endonuclease is a type IIS restriction endonuclease.

44. The kit of claim 39, wherein said first restriction endonuclease is BsgI, and said second restriction endonuclease is FokI.

45. The kit of claim 39, further comprising (a) a third restriction endonuclease that recognizes a sequence consisting of at least 8 bases; and (b) a fourth restriction endonuclease that recognizes a sequence consisting of four bases, wherein digestion of said DNA vector with said third and fourth restriction endonucleases cleaves said DNA vector at said insertion site.

46. A method of identifying gene transcription patterns in an mRNA population, comprising the steps of:

(a) preparing double-stranded cDNAs from a mRNA population using a primer, wherein said primer comprises an oligo dT sequence linked at its 5' end to a NotI cleavage site;

(b) cleaving said double-stranded cDNAs with NotI and with MboI to obtain cDNA inserts;

(c) inserting said cDNA inserts into insertion sites of cloning vectors to obtain DNA constructs, wherein said cloning vectors comprise a BsgI recognition sequence 5' to the insertion sites such that digestion of said DNA constructs with BsgI is capable of cleaving said DNA constructs at sites within the cDNA inserts, and a FokI recognition sequence which is 5' to said BsgI recognition sequence, and wherein said cDNA inserts are inserted into said cloning vectors such that an MboI-cleaved end is proximal to the BsgI recognition sequence and a NotI-cleaved end is distal to the BsgI recognition sequence;

(d) replicating said DNA constructs;

(e) isolating said DNA constructs;

(f) digesting said DNA constructs with BsgI;

(g) digesting said DNA constructs with FokI to obtain tags, wherein said tags comprise a portion of said cDNAs;

(h) treating said tags with T4 DNA polymerase to obtain blunt-ended tags;

(i) ligating said blunt-ended tags using DNA ligase to obtain ligated tandem arrays of tags comprising 30 to 60 tags;

(j) inserting said ligated tandem arrays of tags into a sequencing vector;

(k) sequencing said ligated tandem arrays of tags to determine the nucleotide residue sequence of individual tags; and (h) comparing the sequences of individual tags to known gene sequences to identify gene transcription patterns in said mRNA population.

47. The method of claim 46, wherein sequences of individual tags each consist of a GGATC sequence, containing an MboI recognition sequence, or its reverse complement, depending on a sense or antisense orientation of each tag during ligation, adjacent to ten additional bases of sequence of a transcribed gene.

* * * * *

UNITED STATES PATENT AND TRADEMARK OFFICE
CERTIFICATE OF CORRECTION

PATENT NO. : 5,968,784
DATED : October 19, 1999
INVENTOR(S) : D. G. Spinella and F. G. Sajjadi It is certified that error appears in the above-identified patent and that said Letters Patent is hereby corrected as shown below:

In Column 27...
In Claim 32 (Column 27, line 18), delete "on" and substitute --of--;
in Claim 33 (Column 27, line 24), delete "26" and substitute --29--.

In Column 28...
In Claim 46 (Column 28, line 55), delete "(h)" and substitute --(I)--.

Signed and Sealed this

Eighth Day of August, 2000

Attest:

Attesting Officer

Q. TODD DICKINSON
Director of Patents and Trademarks

SEQUENCE LISTING (1) GENERAL INFORMATION:

(iii) NUMBER OF SEQUENCES:     6

(2) INFORMATION FOR SEQ ID NO: 1:

(i) SEQUENCE CHARACTERISTICS:
      (A) LENGTH:          3737 base pairs

```
        (B) TYPE:           nucleic acid
        (C) STRANDEDNESS:   single
        (D) TOPOLOGY:       linear (xi) SEQUENCE DESCRIPTION: SEQ ID NO: 1:

TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC      180

ACCATATGCG GTGTGAAATA CCGCACAGAT GCGTAAGGAG AAAATACCGC ATCAGGCGCC     240

ATTCGCCATT CAGGCTGCGC AACTGTTGGG AAGGGCGATC GGTGCGGGCC TCTTCGCTAT     300

TACGCCAGCT GGCGAAAGGG GGATGTGCTG CAAGGCGATT AAGTTGGGTA ACGCCAGGGT     360

TTTCCCAGTC ACGACGTTGT AAAACGACGG CCAGTGAATT CGAGCTCGGT ACCGGATGAC     420

ACGTGCAGGA TCCATGATCA TCGTGGCGCA TGTATTACTC ATCCTTTTGG GGGCCACTGA     480

GATACTGCAA GCTGACTTAC TTCCTGATGA AAAGATTTCA CTTCTCCCAC CTGTCAATTT     540

CACCATTAAA GTTACTGGTT TGGCTCAAGT TCTTTTACAA TGGAAACCAA ATCCTGATCA     600

AGAGCAAAGG AATGTTAATC TAGAATATCA AGTGAAAATA AACGCTCCAA AGAAGATGA     660

CTATGAAACC AGAATCACTG AAAGCAAATG TGTAACCATC CTCCACAAAG GCTTTTCAGC     720

AAGTGTGCGG ACCATCCTGC AGAACGACCA CTCACTACTG GCCAGCAGCT GGGCTTCTGC     780

TGAACTTCAT GCCCCACCAG GGTCTCCTGG AACCTCAATT GTGAATTTAA CTTGCACCAC     840

AAACACTACA GAAGACAATT ATTCACGTTT AAGGTCATAC CAAGTTTCCC TTCACTGCAC     900

CTGGCTTGTT GGCACAGATG CCCCTGAGGA CACGCAGTAT TTTCTCTACT ATAGGTATGG     960

CTCTTGGACT GAAGAATGCC AAGAATACAG CAAAGACACA CTGGGGAGAA ATATCGCATG    1020

CTGGTTTCCC AGGACTTTTA TCCTCAGCAA AGGGCGTGAC TGGCTTTCGG TGCTTGTTAA    1080

CGGCTCCAGC AAGCACTCTG CTATCAGGCC CTTTGATCAG CTGTTTGCCC TTCACGCCAT    1140

TGATCAAATA AATCCTCCAC TGAATGTCAC AGCAGAGATT GAAGGAACTC GTCTCTCTAT    1200

CCAATGGGAG AAACCAGTGT CTGCTTTTCC AATCCATTGC TTTGATTATG AAGTAAAAAT    1260

ACACAATACA AGGAATGGAT ATTTGCAGAT AGAAAAATTG ATGACCAATG CATTCATCTC    1320

AATAATTGAT GATCTTTCTA AGTACGATGT TCAAGTGAGA GCAGCAGTGA GCTCCATGTG    1380

CAGAGAGGCA GGGCTCTGGA GTGAGTGGAG CCAACCTATT TATGTGGGAA ATGATGAACA    1440

CAAGCCCTTG AGAGAGTGGT TTGTCGCGGC CGCTCTAGAG TCGACCTGCA GGCATGCAAG    1500

CTTGGCGTAA TCATGGTCAT AGCTGTTTCC TGTGTGAAAT TGTTATCCGC TCACAATTCC    1560

ACACAACATA CGAGCCGGAA GCATAAAGTG TAAAGCCTGG GGTGCCTAAT GAGTGAGCTA    1620

ACTCACATTA ATTGCGTTGC GCTCACTGCC CGCTTTCCAG TCGGGAAACC TGTCGTGCCA    1680

GCTGCATTAA TGAATCGGCC AACGCGCGGG GAGAGGCGGT TTGCGTATTG GCGCTCTTC     1740

CGCTTCCTCG CTCACTGACT CGCTGCGCTC GGTCGTTCGG CTGCGGCGAG CGGTATCAGC    1800

TCACTCAAAG GCGGTAATAC GGTTATCCAC AGAATCAGGG GATAACGCAG AAAGAACAT     1860

GTGAGCAAAA GGCCAGCAAA AGGCCAGGAA CCGTAAAAAG GCCGCGTTGC TGGCGTTTTT    1920

CCATAGGCTC CGCCCCCCTG ACGAGCATCA CAAAAATCGA CGCTCAAGTC AGAGGTGGCG    1980

AAACCCGACA GGACTATAAA GATACCAGGC GTTTCCCCCT GGAAGCTCCC TCGTGCGCTC    2040

TCCTGTTCCG ACCCTGCCGC TTACCGGATA CCTGTCCGCC TTTCTCCCTT CGGGAAGCGT    2100

GGCGCTTTCT CATAGCTCAC GCTGTAGGTA TCTCAGTTCG GTGTAGGTCG TTCGCTCCAA    2160

GCTGGGCTGT GTGCACGAAC CCCCCGTTCA GCCCGACCGC TGCGCCTTAT CCGGTAACTA    2220
```

```
TCGTCTTGAG TCCAACCCGG TAAGACACGA CTTATCGCCA CTGGCAGCAG CCACTGGTAA      2280

CAGGATTAGC AGAGCGAGGT ATGTAGGCGG TGCTACAGAG TTCTTGAAGT GGTGGCCTAA      2340

CTACGGCTAC ACTAGAAGGA CAGTATTTGG TATCTGCGCT CTGCTGAAGC CAGTTACCTT      2400

CGGAAAAAGA GTTGGTAGCT CTTGATCCGG CAAACAAACC ACCGCTGGTA GCGGTGGTTT      2460

TTTTGTTTGC AAGCAGCAGA TTACGCGCAG AAAAAAAGGA TCTCAAGAAG ATCCTTTGAT      2520

CTTTTCTACG GGGTCTGACG CTCAGTGGAA CGAAAACTCA CGTTAAGGGA TTTTGGTCAT      2580

GAGATTATCA AAAAGGATCT TCACCTAGAT CCTTTTAAAT TAAAAATGAA GTTTTAAATC      2640

AATCTAAAGT ATATATGAGT AAACTTGGTC TGACAGTTAC CAATGCTTAA TCAGTGAGGC      2700

ACCTATCTCA GCGATCTGTC TATTTCGTTC ATCCATAGTT GCCTGACTCC CCGTCGTGTA      2760

GATAACTACG ATACGGGAGG GCTTACCATC TGGCCCCAGT GCTGCAATGA TACCGCGAGA      2820

CCCACGCTCA CCGGCTCCAG ATTTATCAGC AATAAACCAG CCAGCCGGAA GGGCCGAGCG      2880

CAGAAGTGGT CCTGCAACTT TATCCGCCTC CATCCAGTCT ATTAATTGTT GCCGGGAAGC      2940

TAGAGTAAGT AGTTCGCCAG TTAATAGTTT GCGCAACGTT GTTGCCATTG CTACAGGCAT      3000

CGTGGTGTCA CGCTCGTCGT TTGGTATGGC TTCATTCAGC TCCGGTTCCC AACGATCAAG      3060

GCGAGTTACA TGATCCCCCA TGTTGTGCAA AAAAGCGGTT AGCTCCTTCG GTCCTCCGAT      3120

CGTTGTCAGA AGTAAGTTGG CCGCAGTGTT ATCACTCATG GTTATGGCAG CACTGCATAA      3180

TTCTCTTACT GTCATGCCAT CCGTAAGATG CTTTTCTGTG ACTGGTGAGT ACTCAACCAA      3240

GTCATTCTGA GAATAGTGTA TGCGGCGACC GAGTTGCTCT TGCCCGGCGT CAATACGGGA      3300

TAATACCGCG CCACATAGCA GAACTTTAAA AGTGCTCATC ATTGGAAAAC GTTCTTCGGG      3360

GCGAAAACTC TCAAGGATCT TACCGCTGTT GAGATCCAGT TCGATGTAAC CCACTCGTGC      3420

ACCCAACTGA TCTTCAGCAT CTTTTACTTT CACCAGCGTT TCTGGGTGAG CAAAAACAGG      3480

AAGGCAAAAT GCCGCAAAAA AGGGAATAAG GGCGACACGG AAATGTTGAA TACTCATACT      3540

CTTCCTTTTT CAATATTATT GAAGCATTTA TCAGGGTTAT TGTCTCATGA GCGGATACAT      3600

ATTTGAATGT ATTTAGAAAA ATAAACAAAT AGGGGTTCCG CGCACATTTC CCCGAAAAGT      3660

GCCACCTGAC GTCTAAGAAA CCATTATTAT CATGACATTA ACCTATAAAA ATAGGCGTAT      3720

CACGAGGCCC TTTCGTC                                                    3737

(2) INFORMATION FOR SEQ ID NO: 2:

(i) SEQUENCE CHARACTERISTICS:
        (A) LENGTH:          670 base pairs
        (B) TYPE:            nucleic acid
        (C) STRANDEDNESS:    single
        (D) TOPOLOGY:        linear (ix) FEATURE:
        (D) OTHER INFORMATION:  The letter "N" stands for A, C,
            T or G. N in positions 6 through 304 may be
            present or absent. N in positions 368
            through 666 may be present or absent.

(xi) SEQUENCE DESCRIPTION: SEQ ID NO: 2:

GATCNNNNNN NNNNNNNNNN NNNNNNNNNN NNNNNNNNNN NNNNNNNNNN NNNNNNNNNN       60

NNNNNNNNNN NNNNNNNNNN NNNNNNNNNN NNNNNNNNNN NNNNNNNNNN NNNNNNNNNN      120

NNNNNNNNNN NNNNNNNNNN NNNNNNNNNN NNNNNNNNNN NNNNNNNNNN NNNNNNNNNN      180

NNNNNNNNNN NNNNNNNNNN NNNNNNNNNN NNNNNNNNNN NNNNNNNNNN NNNNNNNNNN      240

NNNNNNNNNN NNNNNNNNNN NNNNNNNNNN NNNNNNNNNN NNNNNNNNNN NNNNNNNNNN      300

NNNNAAAAAA AAAAAAAAAA AAAGCGGCCG CCATGCATGG CGGCCGCTTT TTTTTTTTTT      360
```

```
TTTTTTNNNN NNNNNNNNNN NNNNNNNNNN NNNNNNNNNN NNNNNNNNNN NNNNNNNNNN        420

NNNNNNNNNN NNNNNNNNNN NNNNNNNNNN NNNNNNNNNN NNNNNNNNNN NNNNNNNNNN        480

NNNNNNNNNN NNNNNNNNNN NNNNNNNNNN NNNNNNNNNN NNNNNNNNNN NNNNNNNNNN        540

NNNNNNNNNN NNNNNNNNNN NNNNNNNNNN NNNNNNNNNN NNNNNNNNNN NNNNNNNNNN        600

NNNNNNNNNN NNNNNNNNNN NNNNNNNNNN NNNNNNNNNN NNNNNNNNNN NNNNNNNNNN        660

NNNNNNGATC                                                               670

(2) INFORMATION FOR SEQ ID NO: 3:

(i) SEQUENCE CHARACTERISTICS:
           (A) LENGTH:          32 base pairs
           (B) TYPE:            nucleic acid
           (C) STRANDEDNESS:    single
           (D) TOPOLOGY:        linear (xi) SEQUENCE DESCRIPTION: SEQ ID NO: 3:

TTTTTTTTTT TTTTTTTTTC GCCGGGCGCA TG                                       32

(2) INFORMATION FOR SEQ ID NO: 4:

(i) SEQUENCE CHARACTERISTICS:
           (A) LENGTH:          15 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for A, C, T
               or G.

(xi) SEQUENCE DESCRIPTION: SEQ ID NO: 4:

GGATCNNNNN NNNNN                                                          15

(2) INFORMATION FOR SEQ ID NO: 5:

(i) SEQUENCE CHARACTERISTICS:
           (A) LENGTH:          20 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for A, C, T
               or G.

(xi) SEQUENCE DESCRIPTION: SEQ ID NO: 5:

GTGCAGGATC NNNNNNNNNN                                                     20

(2) INFORMATION FOR SEQ ID NO: 6:

(i) SEQUENCE CHARACTERISTICS:
           (A) LENGTH:          14 base pairs
           (B) TYPE:            nucleic acid
           (C) STRANDEDNESS:    single
           (D) TOPOLOGY:        linear (ix) FEATURE:
           (D) OTHER INFORMATION:   The letter "N" stands for A, C, T
               or G.

(xi) SEQUENCE DESCRIPTION: SEQ ID NO: 6:

GATCNNNNNN NNNN                                                           14
```